United States Patent
Ryu et al.

(10) Patent No.: US 10,293,081 B2
(45) Date of Patent: May 21, 2019

(54) HIGH-STRENGTH CRYSTALLIZED GLASS CERAMIC COMPRISING WOLLASTONITE, HYDROXYAPATITE AND AKERMANITE

(71) Applicant: BIOALPHA CORPORATION, Seoul (KR)

(72) Inventors: Mi Young Ryu, Gyeonggi-do (KR); Sung Nam Park, Gyeonggi-do (KR); Jun Hyuk Seo, Gyeonggi-do (KR); Hyun Seung Ryu, Gyeonggi-do (KR)

(73) Assignee: BIOALPHA CORPORATION, Seoul (KR)

( * ) Notice: Subject to any disclaimer, the term of this patent is extended or adjusted under 35 U.S.C. 154(b) by 0 days.

(21) Appl. No.: 15/531,442

(22) PCT Filed: May 27, 2015

(86) PCT No.: PCT/KR2015/005284
§ 371 (c)(1),
(2) Date: Jul. 24, 2017

(87) PCT Pub. No.: WO2016/085069
PCT Pub. Date: Jun. 2, 2016

(65) Prior Publication Data
US 2018/0028716 A1 Feb. 1, 2018

(30) Foreign Application Priority Data

Nov. 28, 2014 (KR) .................. 10-2014-0169052
May 19, 2015 (KR) .................. 10-2015-0069925

(51) Int. Cl.
*C03C 10/00* (2006.01)
*A61L 27/10* (2006.01)
(Continued)

(52) U.S. Cl.
CPC ............ *A61L 27/10* (2013.01); *A61L 27/12* (2013.01); *C03C 4/0007* (2013.01); *C03C 10/00* (2013.01);
(Continued)

(58) Field of Classification Search
CPC ..................... C03C 10/00; C03C 10/0009
(Continued)

(56) References Cited

U.S. PATENT DOCUMENTS 4,560,666 A 12/1985 Yoshida et al.
4,871,384 A * 10/1989 Kasuga .................. A61L 27/12
65/30.1
(Continued)

FOREIGN PATENT DOCUMENTS

KR 10-1994-0003461 B1 4/1994

OTHER PUBLICATIONS

Liu. Bioactive glass-ceramic: formation, characterization and bioactivity. MateriaLf Chem&y and P!zysks, 36 (1994) 294-303.*
(Continued)

*Primary Examiner* — Noah S Wiese
(74) *Attorney, Agent, or Firm* — Greer, Burns & Crain, Ltd.; Gregory P. Einhorn

(57) ABSTRACT

The present invention relates to a crystallized glass ceramic comprising 30 wt % to 40 wt % of each of $CaSiO_3$, $Ca_{10}(PO_4)_6(OH)_2$, and $Ca_2Mg(Si_2O_7)$; a crystallized glass ceramic composition comprising $CaSiO_3$, $Ca_{10}(PO_4)_6(OH)_2$, and $Ca_2Mg(Si_2O_7)$ in a predetermined weight ratio; a bone graft material comprising the glass ceramic; and an intervertebral spacer or medical device for replacement of bone tissue, which is manufactured using the bone graft material.

9 Claims, 5 Drawing Sheets

(51) Int. Cl.
*A61L 27/12* (2006.01)
*C03C 4/00* (2006.01)

(52) U.S. Cl.
CPC ....... *C03C 10/0009* (2013.01); *A61L 2430/38* (2013.01); *C03C 2204/00* (2013.01)

(58) Field of Classification Search
USPC .......................................................... 501/2, 5
See application file for complete search history.

(56) References Cited

U.S. PATENT DOCUMENTS

| | | | | |
|---|---|---|---|---|
| 5,232,878 A | * | 8/1993 | Kasuga | A61L 27/12 106/35 |
| 5,344,456 A | * | 9/1994 | Nonami | A61L 27/10 106/35 |
| 5,356,436 A | * | 10/1994 | Nonami | A61L 27/10 106/35 |
| 2005/0079226 A1 | | 4/2005 | Gonda et al. | |
| 2012/0058152 A1 | | 3/2012 | Garcia de Castro Andrews et al. | |

OTHER PUBLICATIONS

Kokubo. Surface Chemistry of Bioactive Glass-Ceramics. Journal of Non-Crystalline Solids 120 (1990) 138-151.*
International Search Report from International Patent Application No. PCT/KR2015/005284, dated Aug. 26, 2015.
Liu et al., "Formation of a New Bioactive Glass-Ceramic," Journal of Materials Science: Materials in Medicine (1994), 5(1), pp. 7-10.
Singh et al., "Bioactivity of Ferrimagnetic MgO—CaO—SiO2—P2O5—Fe2O3 Glass Ceramics," Ceramics International (2010), 36(1), pp. 283-290.
Office Action for Japanese Patent Application JP 2017-547365 dated Jul. 31, 2018.

* cited by examiner

[FIG. 1]
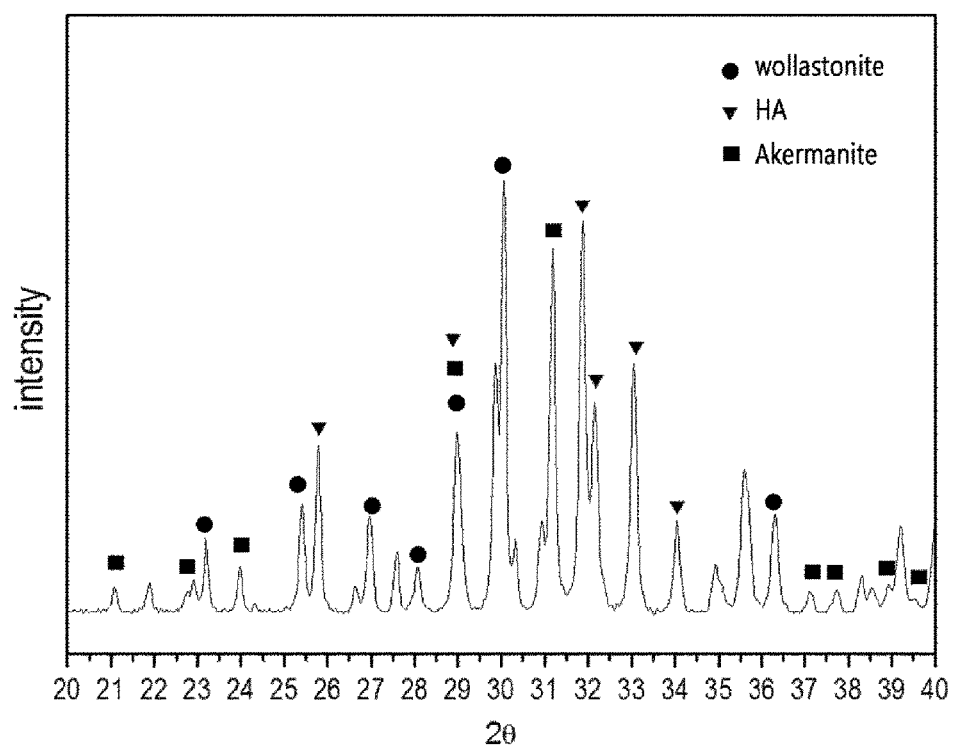

[FIG. 2]
(A) 800°C
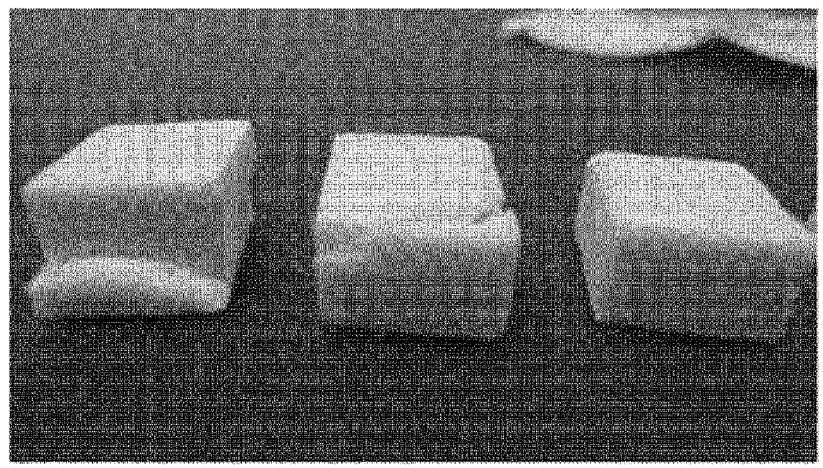
(B) 900°C
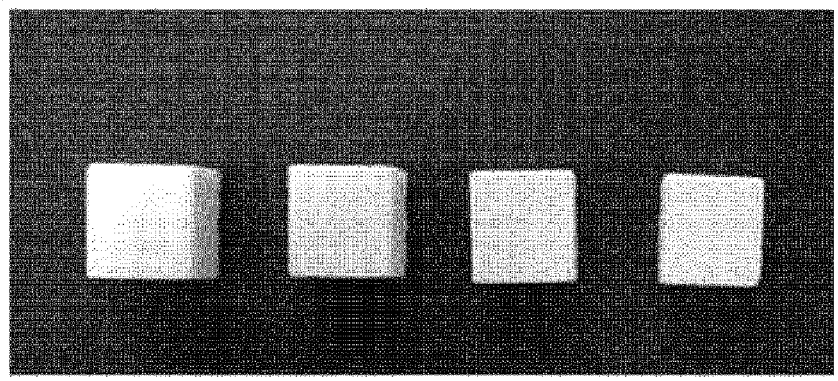

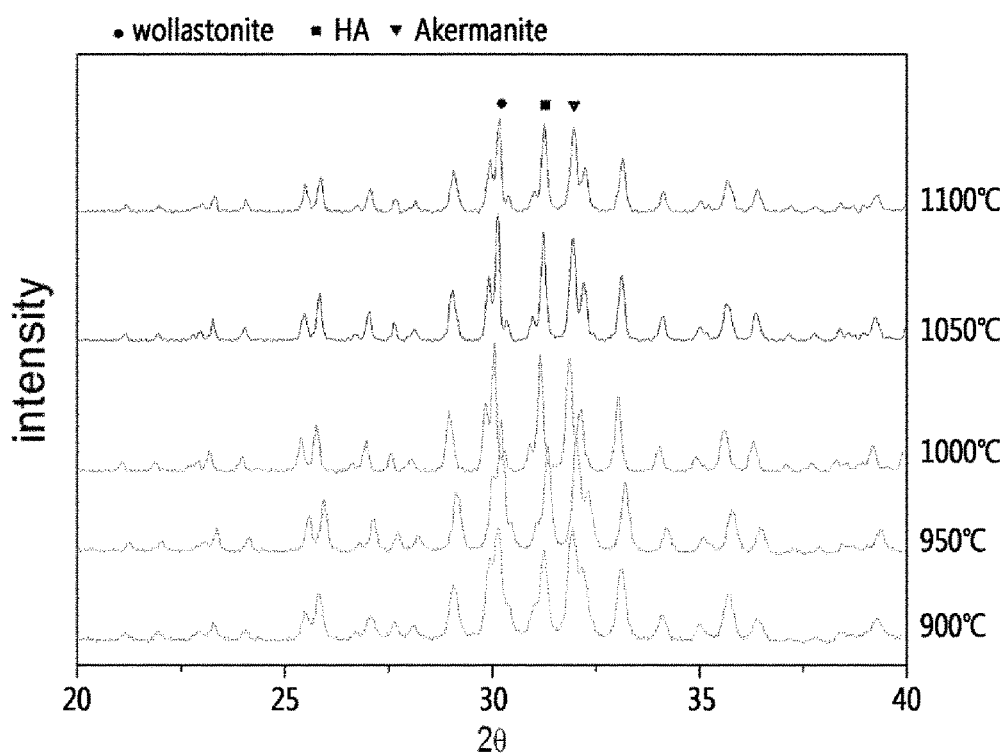
[FIG. 3]

[FIG. 4]
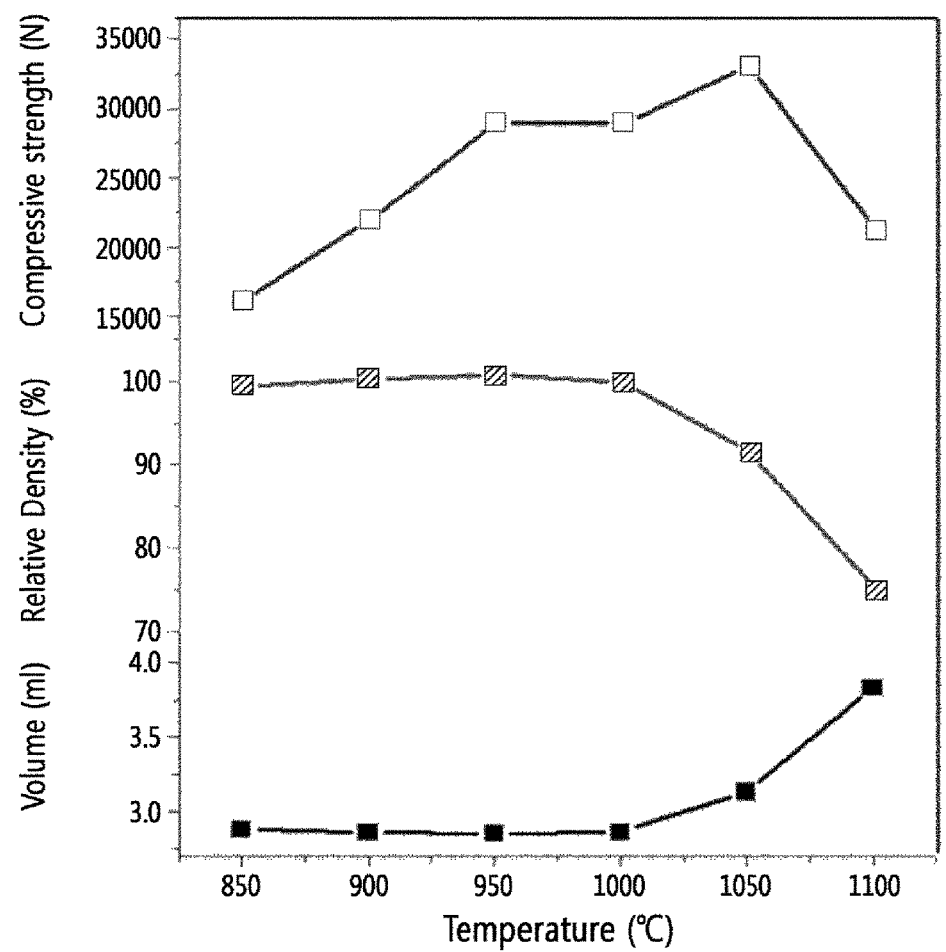

[FIG. 5]
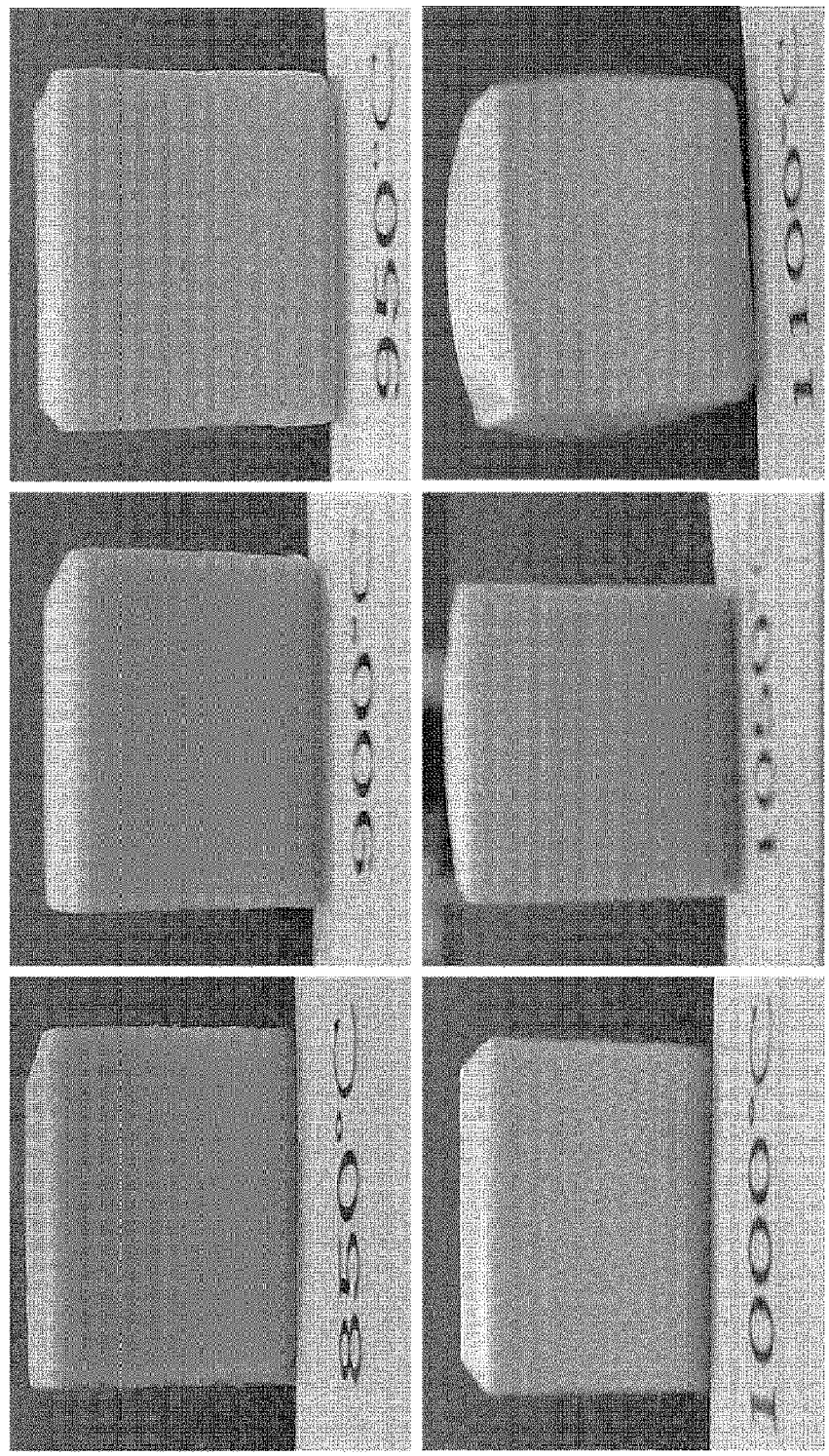

HIGH-STRENGTH CRYSTALLIZED GLASS CERAMIC COMPRISING WOLLASTONITE, HYDROXYAPATITE AND AKERMANITE

RELATED APPLICATIONS

This application is a national phase application claiming benefit of priority under 35 U.S.C. § 371 to International (PCT) Patent Application serial number PCT/KR2015/005284, filed May 27, 2015, which claims benefit of priority to Korean Applications 10-2014-0169052, filed Nov. 28, 2014, and 10-2015-0069925 May 19, 2015. The aforementioned applications are expressly incorporated herein by reference in their entirety and for all purposes.

TECHNICAL FIELD

The present invention relates to a crystallized glass ceramic containing 30 wt % to 40 wt % of each of $CaSiO_3$, $Ca_{10}(PO_4)_6(OH)_2$, and $Ca_2Mg(Si_2O_7)$; a crystallized glass ceramic composition containing $CaSiO_3$, $Ca_{10}(PO_4)_6(OH)_2$, and $Ca_2Mg(Si_2O_7)$ in a predetermined weight ratio; a bone graft material comprising the glass ceramic; and an intervertebral spacer or medical device for replacement of bone tissue, which is manufactured using the bone graft material.

BACKGROUND

Lumber spinal stenosis refers to a medical condition in which the spinal canal or neural tube that encompasses the spinal cord is compressed by a bone or ligament enlarged due to a degenerative change. Such an enlarged bone or ligament presses the nerve that passes through the lumbar spinal canal, thereby causing low back pain or leg pain. Although non-surgical treatment may be performed as a primary treatment, spinal stenosis not responding to non-surgical treatment for a certain period of time can be treated fundamentally only by a surgical operation. Therefore, surgical treatment must be considered in patients who have diseases that have progressed considerably and thus do not show any significant effect by conservative therapies, or patients who have many limitations in daily lives or have acute severe symptoms accompanied by a disc disease.

Examples of the surgical methods of treating the disease may include an intervertebral fusion which uses an intervertebral implant cage and a posterior pedicle screw. The intervertebral fusion often results in removal or destruction of several vertebral elements, such as the lamina and spinous process, and may thus cause structural deformations of the vertebrae and instability of the respective parts. Additionally, since the intervertebral fusion surgery completely restricts the motion of the treatment site, the procedure relatively increases the motion of the adjacent segments and may thereby accelerate the degeneration of the lumbar spine.

An exemplary surgical method to remedy the problem of the intervertebral fusion may be a method of expanding the nerve space under compression by inserting a device between interspinous processes of vertebrae. This method may be used instead of the existing method of removing vertebral bones or discs for the purpose of releasing the compressed nerves. In particular, the device inserted between interspinous processes of vertebrae is an intervertebral spacer and also called interspinous spacer. This method is a surgical method suitable for those patients who have a symptom that becomes severe when bending their waist backward while the symptom is alleviated when bending their waist forward. Upon insertion of the spacer, the ligament or disc that had invaded the intervertebral space is straightened, and thus the nerve-compressing phenomenon is resolved. In addition, with regard to disc diseases in which the disc height is reduced, the neuropores can be widened and thus the method has an effect of preventing spinal stenosis that may occur after simple decompression surgery.

The intervertebral spacer may be manufactured using a material such as metals, ceramics, polymers, etc. The material for the intervertebral spacer may be selected considering strength, durability, biocompatibility, in vivo stability, in vivo non-toxicity, easy processability, disinfection/sterilization stability, etc. Additionally, it is important that the material is provided with magnetic permeability, radiolucency, and appropriate hardness. A metal such as titanium, etc. have excellent biocompatibility and strength, but it has an extremely high modulus of elasticity, and thus may cause a stress shielding effect and also causes an interference phenomenon in response to a strong magnetic field such as MRI, etc., thereby making it difficult to perform a follow-up surveillance after surgery. Meanwhile, polymers such as PEEK have advantages in that they have high-strength, a low risk of fracture, and an appropriate modulus of elasticity but has a disadvantage in that they have significantly low biocompatibility compared to ceramics or metals such as titanium, etc. Ceramics such as hydroxyapatite (HA), bioglass, etc. have high biocompatibility but have low strength and a high risk of fracture, and thus it may be difficult to solely use them.

SUMMARY

The inventors of the present invention have made intensive research efforts to improve the strength while reducing the risk of fracture of ceramics, which are highly-biocompatible materials, for their use as a bone graft material. As a result, they have confirmed that when the ceramic is manufactured using a crystallized glass ceramic composite ($CaSiO_3$, $Ca_{10}(PO_4)_6(OH)_2$, and $Ca_2Mg(Si_2O_7)$), which was obtained by sintering at a high temperature by mixing several kinds of ceramics (e.g., $CaO$—$Si_2O$—$P_2O_5$—$B_2O_3$—$MgO$) in an appropriate weight ratio, the strength of the thus-manufacture ceramic can be significantly improved compared to the conventionally-used wollastonite/hydroxyapatite (HA) composite glass ceramic or hydroxyapatite (HA) sintered body thereby completing the present invention.

TECHNICAL SOLUTION

An object of the present invention is to provide a crystallized glass ceramic comprising 30 wt % to 40 wt % of each of $CaSiO_3$, $Ca_{10}(PO_4)_6(OH)_2$, and $Ca_2Mg(Si_2O_7)$.

Another object of the present invention is to provide a crystallized glass ceramic composition comprising $CaSiO_3$, $C_{10}(PO_4)_6(OH)_2$, and $Ca_2Mg(Si_2O_7)$ at a weight ratio of 30 to 40:30 to 40:30 to 40.

Still another object of the present invention is to provide a bone graft material comprising the above glass ceramic.

Still another object of the present invention is to provide an intervertebral spacer or medical device for replacement of bone tissue manufactured using the above bone graft material.

The bone graft material of the present invention can be effectively used as a material for an intervertebral spacer or a medical device for replacement of bone tissue because the crystallized glass ceramics, which are crystallized by sintering at a high temperature a mixed composition, which further contains Akermanite in addition to $CaSiO_3$ (e.g., wollastonite) and $Ca_{10}(PO_4)_6(OH)_2$ (e.g., hydroxyapatite; HA), has significantly enhanced strength compared to the conventional wollastonite/hydroxyapatite (HA) composite glass ceramics or hydroxyapatite (HA) sintered bodies.

BRIEF DESCRIPTION OF DRAWINGS

FIG. 1 is a graph showing the analysis results of crystal components of the composition according to the present invention.

FIG. 2 is a graph showing the strength of glass ceramics according to sintering temperature. FIGS. 2(A) and 2(B) show images of glass ceramics manufactured by sintering at 800° C. and 900° C., respectively.

FIG. 3 is a graph showing the XRD analysis results for confirming the crystallization of the glass ceramic according to the sintering temperature of the glass ceramic of the present invention.

FIG. 4 is a graph showing the volume, relative density, and compressive strength of the glass ceramic according to the sintering temperature of the glass ceramic of the present invention.

FIG. 5 is a view showing the shapes of sintered bodies according to the sintering temperature of the glass ceramic of the present invention.

DETAILED DESCRIPTION

A first aspect of the present invention provides a crystallized glass ceramic comprising 30 wt % to 40 wt % of each of $CaSiO_3$, $Ca_{10}(PO_4)_6(OH)_2$, and $Ca_2Mg(Si_2O_7)$.

A second aspect of the present invention provides a crystallized glass ceramic composition comprising $CaSiO_3$, $Ca_{10}(PO_4)_6(OH)_2$, and $Ca_2Mg(Si_2O_7)$ at a weight ratio of 30 to 40:30 to 40:30 to 40.

A third aspect of the present invention provides a bone graft material comprising the above glass ceramic.

A fourth aspect of the present invention provides an intervertebral spacer or medical device for replacement of bone tissue manufactured using the above bone graft material.

Hereinafter, the present invention will be described in detail.

The present invention, which is related to the discovery of a novel bone graft composition, is based on the first confirmation of the optimal ratio that can provide the required strength when processed into medical devices such as an intervertebral spacer, etc., by controlling the mixing ratio of $CaSiO_3$, $Ca_{10}(PO_4)_6(OH)_2$, $Ca_2Mg(Si_2O_7)$.

The present invention relates to a crystallized glass ceramic comprising 30 wt % to 40 wt % of each of $CaSiO_3$, $Ca_{10}(PO_4)_6(OH)_2$, and $Ca_2Mg(Si_2O_7)$. Preferably, $CaSiO_3$ may be wollastonite; $Ca_{10}(PO_4)_6(OH)_2$ may be hydroxyapatite (HA); and $Ca_2Mg(Si_2O_7)$ may be Akermanite.

As used herein, the term "wollastonite" is a calcium inosilicate mineral represented by the chemical formula of $CaSiO_3$, which may contain small amounts of iron, magnesium, and manganese instead of calcium. Naturally, wollastonite may be formed when limestones or dolostones with impurities are subjected to high-temperature and high-pressure conditions in the presence of silica-bearing fluids, as in the cases of skarns or contact metamorphic rocks. The relevant minerals may include garnets, vesuvianite, diopside, tremolite, epidote, plagioclase feldspar, pyroxene, and calcite. For example, wollastonite may be produced by reacting silica with calcite, which releases carbon dioxide:

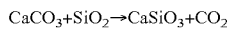

Wollastonite can be used in ceramics, friction products such as brakes and clutches, metalmaking, paint fillers, and plastics. The main countries of wollastonite production are China, India, USA, Mexico, Finland, etc.

As used herein, the term "hydroxyapatite (hereinafter, referred to as HA)" of the present invention is a naturally-occurring mineral form of calcium apatite, which has the chemical formula of $Ca_5(PO_4)_3(OH)$, but it can normally be expressed as $Ca_{10}(PO_4)_6(OH)_2$ because the crystal unit cell contains two independent bodies. Hydroxyapatite refers to a single hydroxy component of a complex apatite group and OH-ion may be substituted with fluoride, chloride, carbonate, etc., to form fluorapatite, chlorapatite, etc. Pure hydroxyapatite powder may be white but natural apatite can be brown, yellow, or green. Hydroxyapatite may be formed naturally or by wet chemical deposition, biomimetic deposition, a sol-gel process which is also referred to as wet chemical precipitation, or electrodeposition. Hydroxyapatite may be present in teeth and bone tissue in the human body. Accordingly, hydroxyapatite may be used as a filler replacing a cut bone tissue or as a coating agent to promote the in-growth of bone tissue into a prosthetic implant.

As used herein, the term "Akermanite", expressed as $Ca_2Mg[Si_2O_7]$, refers to a melilite mineral of the sorosilicate group containing calcium, magnesium, silicon, and oxygen. Akermanite may be formed by contact metamorphism of siliceous limestones and dolostones, and rocks of sanidinite facies. Akermanite ranks a 5 or 6 on the Mohs scale of mineral hardness and may be found gray, green, brown, or colorless. Additionally, Akermanite may have a white streak and a vitreous or resinous luster.

The present invention is characterized in that it provides a material with significantly enhanced strength compared to glass ceramics which contain $CaSiO_3$ and $Ca_{10}(PO_4)_6(OH)_2$, by further comprising $Ca_2Mg(Si_2O_7)$.

Preferably, the crystallized glass ceramic of the present invention may be formed by sintering at a temperature of 850° C. to 1,100° C. When the sintering temperature is less than or equal to 800° C., the crystallized glass ceramic may be damaged due to rapid crystallization, and thus may be impossible to be used as a product. Meanwhile, the sintering temperature over 1,100° C. is undesirable because energy waste due to unnecessary heating is not only accompanied but also mechanical properties of the manufactured ceramic may be deteriorated due to excessive crystallization of the glass component.

For providing glass ceramics with enhanced strength, the present invention provides a crystallized glass ceramic composition comprising $CaSiO_3$, $Ca_{10}(PO_4)_6(OH)_2$, and $Ca_2Mg(Si_2O_7)$ at a weight ratio of 30 to 40:30 to 40:30 to 40.

A bone graft material of the present invention may comprise the above glass ceramic. As described above, for enhancement of strength, the glass ceramic may be manufactured by sintering a crystallized glass ceramic composition, which comprises $CaSiO_3$, $Ca_{10}(PO_4)_6(OH)_2$, and $Ca_2Mg(Si_2O_7)$ at a weight ratio of 30 to 40:30 to 40:30 to 40, at a high temperature. The preferred sintering temperature is the same as described above.

The bone graft material with enhanced strength may be used for manufacturing an intervertebral spacer or medical device for replacement of bone tissue.

In particular, the intervertebral spacer or medical device for replacement of bone tissue is characterized in that it includes the crystallized glass ceramic according to the present invention in an area directly bonded to the surrounding bones. In a specific example of the present invention, it was confirmed that the spacer showed a bonding in a significantly increased area when the spacer made of the glass ceramic material according to the present invention was used, as compared to when the autograft bone was transplanted in a titanium cage (Table 2). Accordingly, in manufacturing the intervertebral spacer or medical device for replacement bone tissue, it is preferred that the glass ceramic according to the present invention, which has excellent compatibility with the surrounding bone tissue after in vivo transplantation, be included in a region in contact with the surrounding bone tissue.

Examples of the international test standards related to the physical/mechanical evaluation of the intervertebral spacer may include ASTM F2077, ASTM F2267, etc. Among them, the former specifies the experimental environment including the jig for the static compression and torsion test and the dynamic fatigue test, and provides related test protocols.

Preferably, the intervertebral spacer or medical device, manufactured using the bone graft material of the present invention, has compressive strength in a range of 3,000 N to 35,000 N or the torsional strength in a range of 0.6 N·m to 1.5 N·m. Additionally, fatigue strength higher than or equal to the maximum compressive strength, which is not broken even after repeating 5,000,000 cycles at a repetition rate of 5 Hz and a stress ratio of 10, may be obtained. Therefore, the intervertebral spacer made of the bone graft of the present invention or medical device for replacement of bone tissue may be used as an intervertebral spacer both for a cervical spine and for a lumbar vertebra requiring higher strength.

As used herein, the term "compressive strength" refers to the maximum stress of a material which can withstand a compressive load. The compressive strength of materials that are broken into pieces upon compression may be defined as an independent nature in a narrow sense, but the compressive strength of materials that are not broken into pieces upon compression may be defined by the amount of stress required to deform any material with a random quantity. The measurement may be made by plotting the force applied to a test device against the deformation. In compression tests, compressive strength may be calculated by dividing the maximum load by the initial cross-sectional area of the specimen.

As used herein, the term "torsional strength or torsion" refers to the degree of capability of a material to withstand a torsional load, in which the torsional strength is the maximum strength of the material subjected to the torsional load, and may be the maximum torsional stress that can maintain the material before fracture, and also called modulus of fracture or shear strength. As the measurement unit, Newton meter (N·m) or feet pound force (ft·lbf) may be used.

As used herein, the term "fatigue strength" refers to the amount of fluctuating stress required for the fracture of a fatigue test specimen by applying a predetermined number of repeated loads, in which the number of repetitions is called fatigue life. Fatigue strength can generally be measured directly from the S—N curve, but is not limited thereto. ASTM defines fatigue strength ($S_{Nf}$) as the stress value at which the fracture of the number of $N_f$ cycles occurs.

For example, the intervertebral spacer or medical device for replacement bone tissue made of the bone graft material according to the present invention may be one manufactured using a bone graft material, which is a dense molded product having a value of relative density corresponding to 95% or higher relative to that of theoretical density, but not limited thereto. When products manufactured using the bone graft material, which is a dense molded product, can provide enhanced strength to be advantageous for withstanding loads, these products may be effectively used as intervertebral spacers or medical devices for replacement of bone tissue.

Hereinafter, the present invention will be described in more detail with reference to the following Examples. However, these Examples are for illustrative purposes only and the invention is not intended to be limited by these Examples.

Example 1: Manufacture and Composition Analysis of High-Strength Crystallized Glass Ceramics $SiO_2$, hydroxyapatite (HA), $Ca(OH)_2$, MgO, $B_2O_3$, $CaF_2$, etc., in the form of powders were boiled at a high temperature of 1,400° C. or higher for 2 hours or more, and then rapidly cooled in water to manufacture raw glass powder. Each raw material was mixed in a ratio of 25 wt % to 35 wt % of $SiO_2$, 25 wt % to 35 wt % of hydroxyapatite (HA), 18 wt % to 22 wt % of $Ca(OH)_2$, 4 wt % to 6 wt % of MgO, 4 wt % to 5 wt % of $B_2O_3$, and 4 wt % to 5 wt % of $CaF_2$. The thus-manufactured glass powder was molded in the same manner as the general method for manufacturing ceramic molded bodies known in the art and then sintered at a high temperature to be crystallized. The crystalline phases obtained by the final crystallization were shown to be mixed with wollastonite, hydroxyapatite and Akermanite in similar proportions. This was analyzed by an X-ray diffraction pattern and the results are shown in FIG. 1. Specifically, 2θ, which is the main diffraction line of each material, was in the range of 29.5° to 30.5° for wollastonite, 31.5° to 32.5° for hydroxyapatite, and 30.5° to 31.5° for Akermanite, and the strength ratio was 36±5%, 33±5%, and 31±5%, respectively.

Example 2: Evaluation of Sintering Characteristics According to Crystallization Temperature To determine the optimum sintering temperature for crystallization of wollastonite, hydroxyapatite, and Akermanite, glass powders of the same composition were sintered at different temperatures to manufacture glass ceramics, and the strength of thus-manufactured glass ceramics was confirmed. Reviewing the sintering tendency of the glass powder according to temperature, the sintering was performed at about 700° C., and when the sintering was performed at this temperature for 2 hours, about 5% of shrinkage occurred. When the sintering was performed at a temperature of 750° C. to 800° C., the glass powder was rapidly crystallized and the linear shrinkage rate reached 18% to 21%. However, when sintering was performed at 750° C., the sintering was performed well, but crystallization of wollastonite did not occur. Meanwhile, it was confirmed that when the sintering was performed at 800°, there was damage on the product due to discontinuation of crystallization (FIG. 2). Therefore, this indicates that the above temperature range is unsuitable for sintering to produce products. When the sintering was performed by further increasing the temperature to 900° C. or higher, it was confirmed that wollastonite was crystallized and the sintering was performed stably without damage on the product. Then, the temperature was increased further and the same crystal phase was maintained up to 1,100° C., indicating that the temperatures up to the above range were suitable for sintering. However, considering the efficiency of the process, the optimum temperature for sintering may be 1,000° C. at which the half-value width of the XRD diffraction peak caused by crystals was significantly reduced (FIG. 3).

Specifically, as shown in FIG. 3, the crystallized glass ceramics according to the present invention, which were manufactured by sintering at 900° C. to 1,100° C., showed three distinct peaks corresponding to each of wollastonite, hydroxyapatite, and Akermanite, which were formed at a similar rate regardless of the temperature, which indicates that the crystal phase was well formed in the above temperature range. When sintered at a temperature of 1,000° C. or higher, the half-width was significantly reduced indicating that an enhanced level of crystallization occurred.

The glass ceramics were manufactured by the method according to the present invention under the same conditions except that they were sintered at a temperature of 850° C. to 1,100° C. in increments of 50° C. within the above temperature range, respectively. The volumes, relative density, and compressive strength of the glass ceramics were measured and shown in Table 1 below, plotted together in the graph, and shown in FIG. 4.

TABLE 1

|  | Volume (mL) | Relative Density (%) | Compressive Strength (N) |
|---|---|---|---|
| 850° C. | 2.8820 | 99.4733 | 16157.95 |
| 900° C. | 2.8603 | 100.3449 | 21963.62 |
| 950° C. | 2.8502 | 100.6912 | 28983.78 |
| 1,000° C. | 2.8631 | 99.8791 | 28940.22 |
| 1,050° C. | 3.1315 | 91.4724 | 33016.09 |
| 1,100° C. | 3.8299 | 74.9538 | 21218.79 |

As shown in FIG. 4, as the sintering temperature increased to 1,000° C. or higher, the relative density began to decrease along with the increase in volume. The compressive strength showed the maximum value at 1,050° C. and gradually decreased at or below 1,050° C. However, all of the compressive strength exceeded 16,000 N in the sintering temperature range of 850° C. to 1,100° C.

Additionally, the final shape of the hexahedral sintered bodies of glass ceramics manufactured by sintering at each of the above temperatures were photographed and shown in FIG. 5. As shown in FIG. 5, it was confirmed that the glass ceramics manufactured by sintering at a temperature of 1,050° C. or higher had a somewhat convex external shape at the middle portion of the surface. From these results, it is possible to find sintering conditions which provide a combination of volume, relative density, and compressive strength suitable for the use of the glass ceramics. For example, for use of the glass ceramics as a bone graft material, the sintering temperature of 1,000° C., at which compressive strength was high and no external change (i.e., no volume expansion) occurred, was selected.

Example 3: Measurement of Strength of Bone Graft Material According to the Present Invention The strength of the bone graft material, which contains a high-strength crystalline glass ceramic comprisings wollastonite, hydroxyapatite, and Akermanite at a predetermined ratio according to the present invention, was measured and compared to the values of the wollastonite/HA composite (i.e., an existing glass ceramic material) and HA (i.e., a bioceramic sintered body).

The wollastonite/HA composite glass ceramic, which was manufactured by molding and sintering at 1,000° C. of the glass powders manufactured using $SiO_2$, hydroxyapatite, and $Ca(OH)_2$ as raw materials, and a HA sintered body, which was manufactured by sintering 100% hydroxyapatite at 1,200° C., were used as Comparative Examples. The strength of the crystalline glass ceramics of the present invention manufactured according to Example 1 and the two kinds of Comparative Examples was measured, and the results of comparison and analysis are shown in Table 2 below. The final sintered body was manufactured as a 1 cm-long cube and the faces were homogenized by polishing to minimize errors in the measurement of strength.

TABLE 2

| Classification | Compressive Strength (MPa) | Flexural Strength (MPa) | Fracture Toughness $(MPa \cdot m^{1/2})$ |
|---|---|---|---|
| Wollastonite/HA Composite Glass Ceramic | 1103 ± 94 | 180 ± 10 | 1.54 ± 0.07 |
| HA Sintered Body | 832 ± 35 | 53 ± 1 | 1.51 ± 0.03 |
| Crystalline Glass Ceramic of Example 1 | 1321 ± 40 | 253 ± 13 | 3.0 ± 0.17 |

As shown in Table 2 above, the bone graft material according to the present invention, which contains a high-strength crystalline glass ceramic comprising wollastonite, hydroxyapatite, and Akermanite, has increased compressive strength by about 20% and 60%, and increased flexural strength by about 40% and 375%, compared to those of the wollastonite/HA composite (i.e., an existing glass ceramic material) and HA (i.e., a bioceramic sintered body), respectively. Additionally, the bone graft material according to the present invention showed significantly increased fracture toughness (i.e., about a 2-fold increase) compared to those of the wollastonite/HA composite and HA, respectively.

Example 4: Manufacture of Intervertebral Spacer Using Crystalline Glass Ceramic According to the Present Invention and Analysis of Characteristics Thereof An intervertebral spacer for a cervical spine can be manufactured by processing the high-strength crystallized glass ceramic material according to the present invention to have compressive strength of 3,000 N or higher, whereas an intervertebral spacer for a lumbar vertebra can be manufactured by processing the high-strength crystallized glass ceramic material according to the present invention to have compressive strength of 8,000 N or higher. That is, as confirmed in Example 2 above, the high-strength crystallized glass ceramic material according to the present invention exhibited compressive strength of about 1,321 MPa. Therefore, it was confirmed that the high-strength crystallized glass ceramic material can theoretically meet the requirements as an intervertebral spacer for a cervical spine and for a lumbar vertebra when manufactured to a size of 2.27 $mm^2$ and 6.06 $mm^2$, respectively. Additionally, it was confirmed that considering that general vertebral spacers have a length, width, and/or depth in the range of several mm to several cm, the crystallized glass ceramic material of the present invention can meet the required strength as an intervertebral spacer for a cervical spine and for a lumbar vertebra suggested above.

Additionally, it was confirmed that the spinal spacer manufactured using the crystallized glass ceramic material according to the present invention had fatigue strength without damage even when the spacer was over 5 million cycles at a repetition rate of 5 Hz and a stress ratio of 10 and when subjected to an additional load with the maximum compressive strength. Furthermore, the torsional strength of the spacer was measured and confirmed to have a value of 0.6 N·m or higher.

The results of clinical tests performed in the human body using the spinal spacer manufactured from the crystallized glass ceramic material according to the present invention showed that the spinal spacer had a binding force with the neighboring bones similar to that of a case where an autograft bone was transplanted to a titanium cage (control group), which is a general surgery method. Among the 39 subjects in whom the corresponding spacer was transplanted to the lumbar region, 35 subjects (89.7%) had been showing excellent clinical results for 12 months and the transplanted spacer directly bonded to the neighboring vertebral body. In particular, as a result of calculating the bonded area between the vertebral body and the spacer, as shown in Table 2 below, the bonded area of the crystallized glass ceramic material according to the present invention to the spacer was statistically significantly higher than that of the autograft bone filled in the titanium cage (p<0.001). The calculated area of the spacer or autograft bone associated with the calculated vertebral endplates was compared as shown in Table 3.

TABLE 3

| Classification | Upper Vertebral Endplate | Lower Vertebral Endplate |
| --- | --- | --- |
| Example 1 | 86.0 ± 48.0 mm² | 81.4 ± 48.6 mm² |
| Control Group | 36.4 ± 16.1 mm² | 39.3 ± 14.7 mm² |

The invention claimed is:

1. A crystallized glass ceramic comprising $CaSiO_3$, $Ca_{10}(PO_4)_6(OH)_2$, and $Ca_2Mg(Si_2O_7)$ at a weight ratio of 30 to 40:30 to 40:30 to 40.

2. The crystallized glass ceramic of claim 1, wherein CaSiO3 comprises a wollastonite, $Ca_{10}(PO_4)_6(OH)_2$ comprises a hydroxyapatite (HA), and $Ca_2Mg(Si_2O_7)$ comprises an akermanite.

3. The crystallized glass ceramic of claim 1, wherein the crystallized glass ceramic has increased compressive strength or flexural strength compared to glass ceramics comprising $CaSiO_3$ and $Ca_{10}(PO_4)_6(OH)_2$ due to $Ca_2Mg(Si_2O_7)$.

4. The crystallized glass ceramic of claim 1, wherein the crystallized glass ceramic is formed by sintering at a temperature of about 850° C. to about 1,100° C.

5. The crystallized glass ceramic of claim 1, which is manufactured by sintering a glass ceramic composition, wherein the glass ceramic composition is manufactured by a process comprising boiling a raw composition comprising $SiO_2$, hydroxyapatite, $Ca(OH)_2$, MgO, $CaF_2$, and $B_2O_3$, wherein the raw composition comprises $SiO_2$ hydroxyapatite, $Ca(OH)_2$, MgO, $CaF_2$ at a weight ratio of 25 to 35:25 to 35:18 to 22:4 to 6:4 to 5.

6. A bone graft material comprising the glass ceramic according to claim 1.

7. An intervertebral spacer or medical device for replacement of bone tissue: manufactured using the bone graft material of claim 6; or, comprising the bone graft material of claim 6.

8. The intervertebral spacer or medical device of claim 7, wherein the intervertebral spacer or medical device has compressive strength in a range of about 3,000 N to about 35,000 N or the torsional strength in a range of about 0.6 Nm to about 1.5 Nm.

9. The intervertebral spacer or medical device of claim 7, wherein the intervertebral spacer or medical device is manufactured using a bone graft material, wherein the bone graft material comprises a dense molded product having a value of relative density corresponding to about 95% or higher relative to that of theoretical density.

* * * * *